(12) United States Patent
Kakileti et al.

(10) Patent No.: US 12,343,116 B2
(45) Date of Patent: Jul. 1, 2025

(54) SYSTEM AND METHOD FOR IDENTIFYING ERRORS IN POSITIONING OF A SUBJECT FOR CAPTURING A THERMAL IMAGE

(71) Applicant: Niramai Health Analytix Pvt Ltd, Bengaluru (IN)

(72) Inventors: Siva Teja Kakileti, Kakinada (IN); Geetha Manjunath, Bengaluru (IN)

(73) Assignee: NIRAMAI HEALTH ANALYTIX PVT. LTD, Bangalore (IN)

( * ) Notice: Subject to any disclaimer, the term of this patent is extended or adjusted under 35 U.S.C. 154(b) by 502 days.

(21) Appl. No.: 17/636,144

(22) PCT Filed: Oct. 17, 2020

(86) PCT No.: PCT/IN2020/050889
§ 371 (c)(1),
(2) Date: Feb. 17, 2022

(87) PCT Pub. No.: WO2021/074929
PCT Pub. Date: Apr. 22, 2021

(65) Prior Publication Data
US 2022/0287570 A1  Sep. 15, 2022

(30) Foreign Application Priority Data
Oct. 18, 2019 (IN) .............................. 201941042222

(51) Int. Cl.
| | |
|---|---|
| A61B 5/01 | (2006.01) |
| A61B 5/00 | (2006.01) |
| G06T 7/73 | (2017.01) |

(52) U.S. Cl.
CPC ............ *A61B 5/015* (2013.01); *A61B 5/4312* (2013.01); *G06T 7/73* (2017.01); *G06T 2207/10048* (2013.01); *G06T 2207/30068* (2013.01)

(58) Field of Classification Search
CPC ..... A61B 5/015; A61B 5/0008; A61B 5/0013; A61B 5/0077; A61B 5/0091;
(Continued)

(56) References Cited

U.S. PATENT DOCUMENTS

2008/0025592 A1* 1/2008 Jerebko ................. G06T 11/005
382/132
2017/0245762 A1* 8/2017 Kakileti ................. B25J 19/023
(Continued)

*Primary Examiner* — Jeffrey G Hoekstra
*Assistant Examiner* — Nicholas A Robinson

(57) ABSTRACT

A method for identifying errors associated with subject positioning in a thermal image of a subject and determining, applying a positional adjustment for adaptive positioning of the subject for capturing a new adjusted thermal image. The method includes (i) receiving an initial thermal image of body of a subject, (ii) automatically segmenting breast region from the initial thermal image, (iii) computing a plurality of positions and a plurality of deviations in the plurality of positions using a thermal imaging protocol, (iv) determining a positional adjustment to be made to a position of thermal imaging camera or a position of the subject based on the plurality of deviations in the plurality of positions of the breast region and (v) applying the positional adjustment for adjusting a position of the thermal imaging camera or subject for capturing a new adjusted thermal image at the required position as per thermal imaging protocol.

15 Claims, 11 Drawing Sheets

(58) Field of Classification Search
CPC ....... A61B 5/7267; G06T 7/0012; G06T 7/11; G06T 7/12; G06T 7/13; G06T 7/70; G06T 2207/10048; G06T 2207/20081; G06T 2207/30068; G06T 2207/30096; G06T 2207/30196; G06T 2207/30244; G06T 2207/20084; G06T 7/73; H04N 23/64; H04N 23/695; H04N 23/23; H04N 23/63; H04N 23/951

See application file for complete search history.

(56) References Cited

U.S. PATENT DOCUMENTS

| | | | |
|---|---|---|---|
| 2017/0249738 A1* | 8/2017 | Sivakumar | G16H 30/20 |
| 2017/0270659 A1* | 9/2017 | Venkataramani | G06T 7/11 |
| 2018/0000461 A1* | 1/2018 | Venkataramani | A61B 5/4312 |
| 2018/0000462 A1* | 1/2018 | Venkataramani | G06T 7/11 |

* cited by examiner

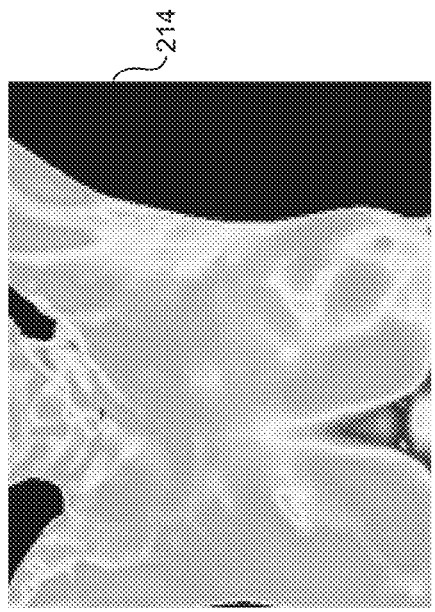
FIG. 2B
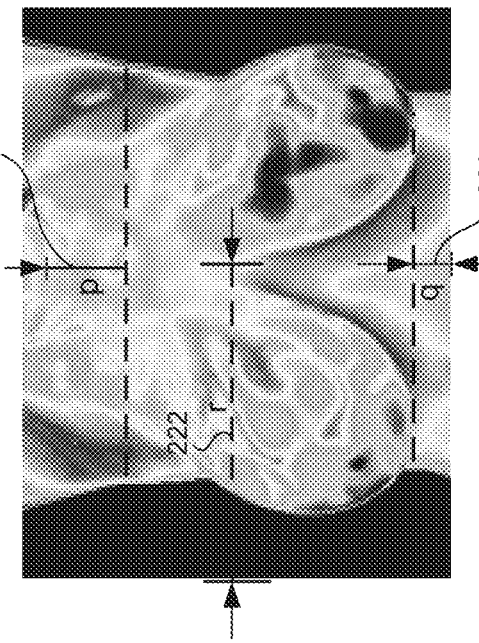
FIG. 2C
FIG. 2E
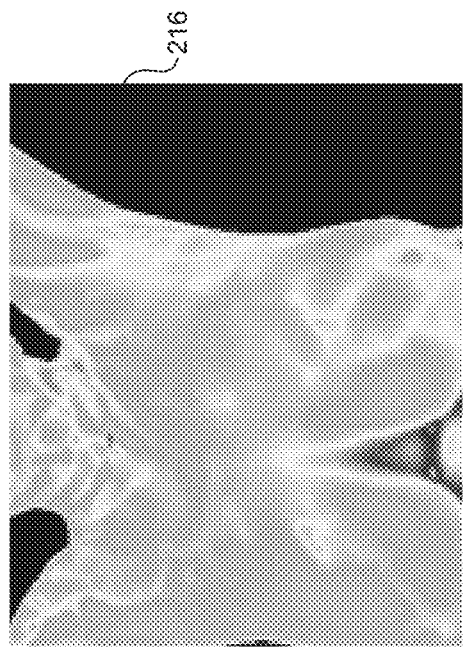
FIG. 2D

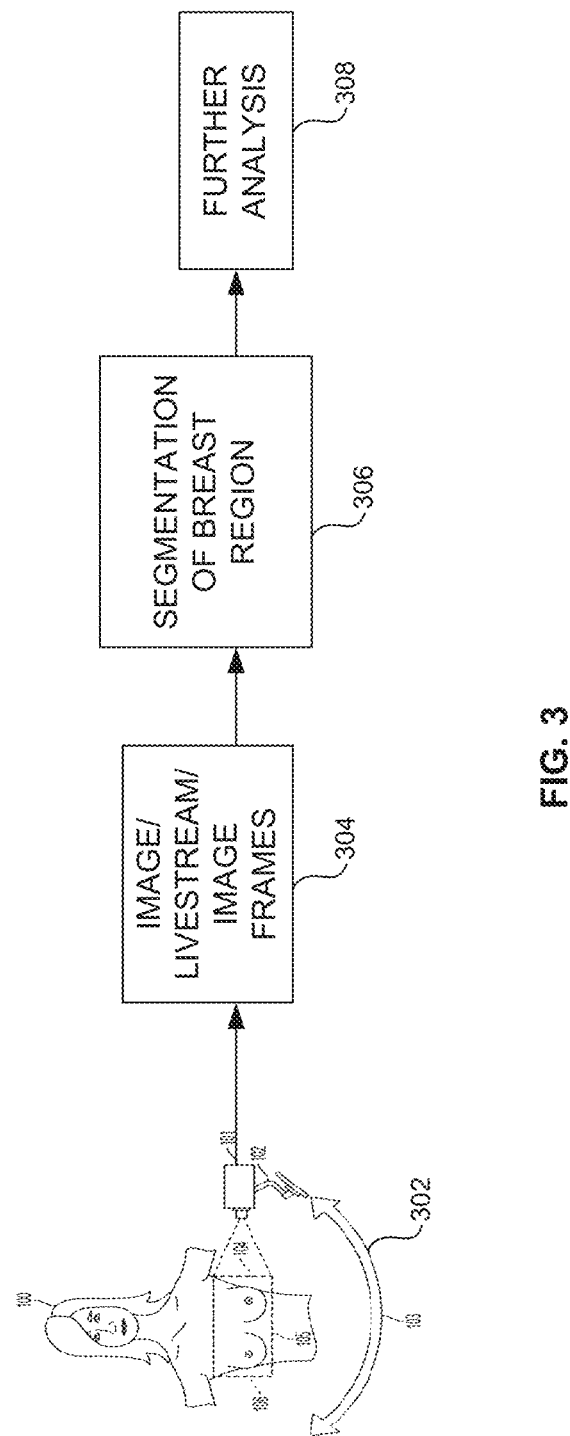

SYSTEM AND METHOD FOR IDENTIFYING ERRORS IN POSITIONING OF A SUBJECT FOR CAPTURING A THERMAL IMAGE

BACKGROUND

Technical Field

Embodiments herein are directed towards capturing thermal image conformant to the standard operating procedure and, more particularly, to a system and method for identifying errors associated with subject positioning in a thermal image and determining, applying a positional adjustment for adaptive positioning of the subject for capturing a new adjusted thermal image.

Description of the Related Art

Breast Cancer is among the leading cause of cancer deaths around the world, especially in women. Though, mammography is considered as a gold standard for detecting breast cancer, it is not affordable to economically backward population. Further, mammography has its own disadvantage of pain due to the compression of the breast and radiation exposure. In recent years, thermography is emerging as a promising modality for detecting breast cancer. Thermography captures the amount of heat radiating from the surface of the body and measures the temperature patterns and distribution on the chest due to high metabolism associated with tumorous growth. There are several advantages of Breast thermography compared to other methods. The breast thermography works on women of all age groups, does not involve any radiation and non-contact, hence painless. The key challenge in breast thermography is that the correctness of interpretation greatly depends upon adherence to protocol during thermal image capture, specifically subject preconditioning and correct capture of thermal images of the patient. Breast thermography requires expertise to capture the images properly as per the protocol. Any error in the image capture could lead to misinterpretation of the images. For example, (i) subject could be too far and hence the region of interest in the image may be in low resolution which may result in loss of information and affect the accuracy of prediction. (ii) subjects could be too close that some portion of the breast region is cut/invisible in the image leading to false negatives and (iii) subjects are not centered in the image leading to inconsistency in image capture across the technicians. Also, there would be a variation in the captured portion of the body across the technicians. In order to make breast thermography usable in large scale population screening programs, such errors have to be minimized as the tool will be used by health workers with the operation skills.

Hence, there is a need for an automated guidance system or method to automatically identify errors associated with subject positioning and provide feedback to a technician for corrective subject positioning for capturing a thermal image.

SUMMARY

In view of the foregoing, an embodiment herein provides a method for identifying errors associated with a subject positioning in a thermal image of a subject and determining, applying a positional adjustment for adaptive positioning of the subject for capturing a new adjusted thermal image. The method includes (i) receiving an initial thermal image of a body of a subject, which represents the temperature distribution on the body of the subject as pixels in the initial thermal image with a highest temperature value being displayed in a first color and pixels with a lowest temperature value being displayed in a second color, pixels with temperature values between the lowest and highest temperature values being displayed in gradations of color between the first and second color, (ii) automatically determining a breast region in the initial thermal image by segmenting the breast region from the initial thermal image using an automated segmentation technique, (iii) computing a plurality of positions (p,q,r) of the breast region with respect to the initial thermal image with a segmentation map, (iv) computing a plurality of deviations (dp, dq, dr) in the plurality of positions of the breast region by comparing the plurality of positions of the breast region with a required position as per thermal imaging protocol, (v) determining, using a machine learning model, a positional adjustment to be made to a position of thermal imaging camera or a position of the subject based on the plurality of deviations (dp, dq, dr) in the plurality of positions of the breast region and (vi) applying the positional adjustment to the thermal imaging camera or the subject to adjust a position of the thermal imaging camera or subject for capturing a new adjusted thermal image at the required position as per the thermal imaging protocol.

The initial thermal image is captured by a thermal imaging camera that includes an array of sensors, a lens and a specialized processor. The array of sensors converts an infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the intial thermal image. The automated segmentation technique segments the thermal image to predict the segmentation map on the initial thermal image The position p is a normalized length of visible region above the breast region in the initial thermal image, the position q is a normalized length of visible region below the breast region in the initial thermal image and the position r is a distance of the breast region from either of a first or a last pixel column of the initial thermal image. The deviation dp is a deviation with respect to visible region above the breast region, the deviation dq is a deviation with respect to visible region below the breast region and the deviation dr is a deviation with respect to the distance of the breast region from either the first or the last pixel column of the initial thermal image.

In an embodiment, the positional adjustment includes at least one of (i) adjusting at least one of the thermal imaging camera, or the subject chair up or down to capture the new adjusted thermal image to obtain correct visible region above the breast region (p) and a part of visible region below the breast region (q) is as per the thermal imaging protocol, (ii) adjusting at least one of the thermal imaging camera, the subject or the subject chair front/back to capture the new adjusted thermal image to obtain correct visible region above the breast region (p) and the part of visible region below the breast region (q) is as per the thermal imaging protocol and (iii) adjusting at least one of the thermal imaging camera, the subject or the subject chair sideways with the distance of the breast region from either of the first or the last pixel column (r) is as per the thermal imaging protocol.

In yet another embodiment, the automated segmentation technique to segment the breast area of the subject in the thermal image includes the steps of (i) determining an outer side contour of an outline of a boundary of the breast area of the subject from a body silhouette, (ii) determining an inner side boundary of the breast area from the body silhouette and the view angle of the initial thermal image, (iii) determining an upper boundary of the breast area by determining a lower boundary of an isotherm of axilla of the subject, (iv) determining a lower boundary of the breast area by determining an upper boundary of an isotherm of inframammary fold of the person and (v) segmenting the breast area of the subject by connecting above determined breast boundaries to segment the breast from surrounding tissue in the initial thermal image.

In yet another embodiment, the automated segmentation technique includes the steps of (i) training a deep learning model by providing a plurality of thermal images as an input and the corresponding segmentation as an output to obtain a trained deep learning model and (ii) providing the new adjusted thermal image to the trained deep learning model to predict the segmentation map.

In yet another embodiment, the set of instructions is provided to at least one of a robotic arm holding the camera, an electronically controlled camera stand or an electronically controlled rotating chair to automatically position itself to the suggested position adjustment for capturing the new adjusted thermal image of the subject as per thermal imaging protocol. The set of instructions are generated by the machine learning model based on the positional adjustment to be made.

In yet another embodiment, the position adjustment is provided to automatically adjust the position of the thermal imaging camera to capture the new adjusted thermal image at the required position without the user's intervention.

In yet another embodiment, the method includes the step of displaying at least one of the position adjustment or the segmented breast region on a visualization screen.

In yet another embodiment, the segmentation and the position deviation are computed for a thermal image obtained by selecting a single image frame of a thermal video or a livestream thermal video. The thermal video or the livestream thermal video is captured using the thermal imaging camera.

In yet another embodiment, the set of instructions includes at least one of a text, a visual or audio for capturing the new adjusted thermal image at the required position as per the thermal imaging protocol.

In yet another embodiment, the method comprises automatic identification of a posture and a position of the subject in the thermal image. The method includes (i) receiving the initial thermal image of a body of a subject, which represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second color, (ii) automatically determining key physical structures and contours of the body in the initial thermal image using an automated segmentation technique and an edge detection technique. The key physical structures and the contours of the body are represented as image points to define a reference body coordinate system in an n-dimensional Euclidean space. (iii) assembling each image point in the Euclidean coordinate system to define the posture and the position of the body; (iv) determining the n-dimensional Euclidian axis (X1-Xn) for a particular posture of interest to define the reference body coordinate system. Each Euclidian axis includes values associated with a physical structure or contour of the body. The values of each Euclidian axis (Xi=1–N) represents a relative distance of the respective physical structure or contour of the body from the boundaries of the initial thermal image, and (v) providing N ordinal values along each corresponding n-dimensional Euclidian axis for the initial thermal image as a numerical representation of the subject's posture and position and a point in an Euclidian space to enable the user to perform further analysis.

The initial thermal image is captured by a thermal imaging camera that includes an array of sensors, a lens and a specialized processor. The array of sensors converts an infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the initial thermal image.

In another aspect, a system for identifying errors associated with a subject positioning in a thermal image of a subject and determining, applying a positional adjustment for adaptive positioning of the subject for capturing a new adjusted thermal image is provided. The system includes a storage device, and a processor retrieving machine-readable instructions from the storage device which, when executed by the processor, enable the processor to (i) receive an initial thermal image of a body of a subject, which represents the temperature distribution on the body of the subject as pixels in the initial thermal image with a highest temperature value being displayed in a first color and pixels with a lowest temperature value being displayed in a second color, pixels with temperature values between the lowest and highest temperature values being displayed in gradations of color between the first and second color, (ii) automatically determine abreast region in the initial thermal image by segmenting the breast region from the thermal image using an automated segmentation technique, (iii) compute a plurality of positions (p,q,r) of the detected breast region segment with respect to the initial thermal image, (iv) compute a plurality of deviations (dp, dq, dr) in the plurality of positions of the detected breast region comparing the plurality of positions of the breast region with to a required position as per thermal imaging protocol, (v) determine a positional adjustment to be made to a position of thermal imaging camera or a position of the subject based on the plurality of deviations (dp, dq, dr) in the plurality of positions of the breast region segment using a machine learning model and (vi) applying the positional adjustment to the thermal imaging camera or the subject to adjust a position of the thermal imaging camera or the subject for capturing a new adjusted thermal image as per the thermal imaging protocol.

The thermal imaging camera includes an array of sensors, a lens and a specialized processor. The array of sensors converts an infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the initial thermal image. In one embodiment, the position p is a normalized length of visible region above the breast region in the initial thermal image, the position q is a normalized length of visible region below the breast region in the initial thermal image and the position r is the distance of breast region from either of a first or a last pixel column of the initial thermal image. In another embodiment, the deviation dp is a deviation with respect to visible region above the breast region, the deviation dq is a deviation with respect to visible region below the breast region and the deviation dr is a deviation with respect to the distance of the breast region from either the first or the last pixel column of the initial thermal image.

In an embodiment, the system implements the position adjustment by (i) adjusting at least one of the thermal imaging camera, or a chair up or down to capture a new adjusted thermal image with an amount of visible region above the breast region (p) and an amount of visible region below the breast region (q) is as per the thermal imaging protocol, (ii) adjusting at least one of the thermal imaging camera, a subject or a chair front/back to capture the new adjusted thermal image with the amount of visible region above the breast region (p) and the amount of visible region below the breast region (q) is as per the thermal imaging protocol, and (iii) adjusting at least one of the thermal imaging camera, a subject or a chair sideways with the distance of the breast region from either of the first or the last pixel column (r) is as per the thermal imaging protocol.

In another embodiment, the system provides the new adjusted captured thermal image and the segmented breast region along with positional adjustment for an automatic tumor detection and automatic tumor classification to detect cancerous tissue and non-cancerous tissue within the breast area of the subject.

In yet another embodiment, the system provides the detected breast region segment in the initial thermal image for an automatic tumor detection or an automatic tumor classification to detect cancerous tissue and non-cancerous tissue within the breast region of the subject, if the plurality of deviations does not exceed a threshold value as per the thermal imaging protocol.

In yet another embodiment, the system provides a set of instructions to at least one of a robotic arm holding the camera, an electronically controlled camera stand or an electronically controlled rotating chair to automatically position itself to the suggested position adjustment for capturing the new adjusted thermal image of the subject as per thermal imaging protocol. The set of instructions are generated by the machine learning model based on the positional adjustment determined by the machine learning model.

The system and method may detect the errors in the captured position and guide the technician for proper capture of the subject. The system and method standardize the image capture protocol for identifying errors associated with subject positioning in a thermal image from a user and generating the feedback to enable the user for adaptive positioning of the subject for capturing a new thermal image. The system and method automate the image capture by sending the feedback to the technician or enable the auto adjustment with the robotic arm/chair. The system and method allow for automated Image Analysis with minimal or no human intervention.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2B-2E illustrate exemplary thermal images processed by an automated segmentation technique to determine a breast region in the thermal images of a subject according to an embodiment herein;

FIG. 3 illustrates an exemplary process flow of an automated Region of Interest (ROI) analysis of a thermal image from a user using a corrective positioning system according to an embodiment herein;

DETAILED DESCRIPTION OF PREFERRED EMBODIMENTS

Figure 1:
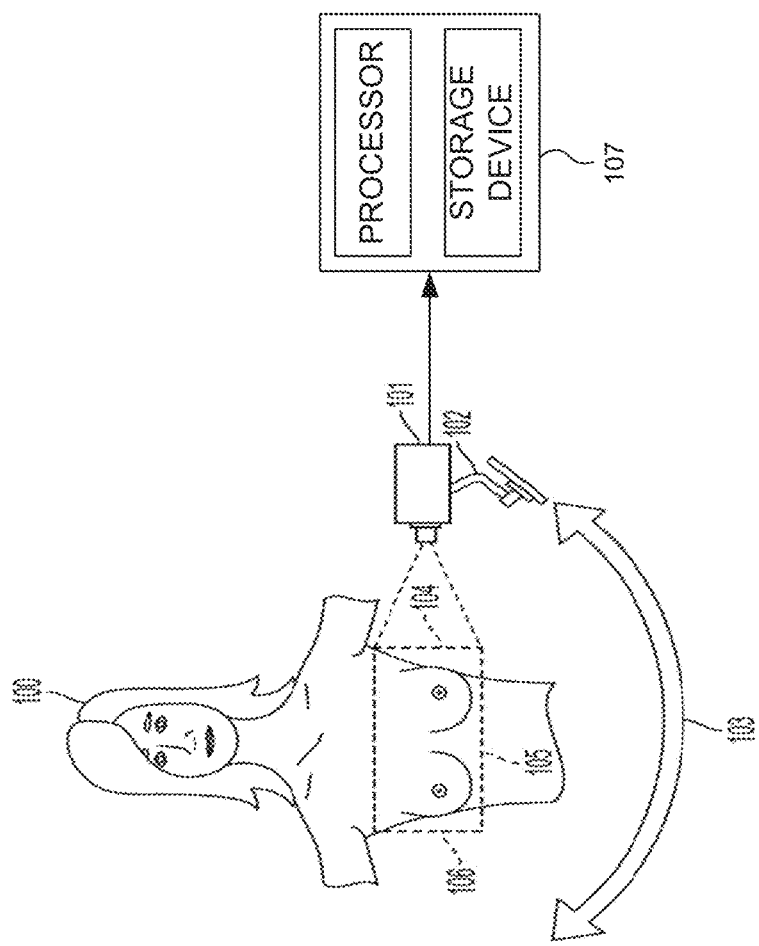
FIG. 1 illustrates an example female patient with a thermal imaging camera mounted on a slidable and axially rotatable robotic arm for moving the thermal camera along a semi-circular trajectory from side-to-side in front of the female patient according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system and a method for identifying errors associated with a subject positioning in a thermal image from a user and generating a feedback to enable the user for adaptive positioning of the subject for capturing a new thermal image. Referring now to the drawings, and more particularly to FIGS. 1 through 8, where similar reference characters denote corresponding features consistently throughout the figures, there are shown preferred embodiments.

A "person" refers to either a male or a female. Gender pronouns are not to be viewed as limiting the scope of the appended claims strictly to females. Moreover, although the term "person" or "patient" is used interchangeably throughout this disclosure, it should be appreciated that the person undergoing breast cancer screening may be something other than a human such as, for example, a primate. Therefore, the use of such terms is not to be viewed as limiting the scope of the appended claims to humans.

A "breast area" refers to a tissue of the breast and may further include surrounding tissue as is deemed appropriate for breast cancer screening. Thermal images are the capture of the breast area in various view angles which include a mediolateral view (centre chest), a mediolateral oblique (angular) view, and a lateral (side) view, as are generally understood in the medical imaging arts. It should be appreciated that the mediolateral view is a supplementary mammographic view which generally shows less breast tissue and pectoral muscle than the mediolateral oblique view. FIG. 1 shows the breast area of a female 100. It should be appreciated that the patient may be stationary while the camera moves about the patient, or the patient can move while the camera remains stationary, or the patient and the camera may move to capture the appropriate view angles as desired.

A "sternum" refers to a long flat breastbone located in the central part of the chest. It connects to the ribs via cartilage and forms the front of the rib cage, thus protects the heart, lungs, and major blood vessels.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colours that correspond to temperatures of the objects in the image.

A "thermographic image" or simply a "thermal image" is an image captured by a thermal camera. The thermographic image comprises an array of color pixels with each color being associated with temperature. Pixels with a higher temperature value are displayed in the thermal image in a first color and pixels with a lower temperature value are displayed in a second color. Pixels with temperature values between the lower and higher temperature values are displayed in gradations of color between the first and second colors.

"Receiving a thermal image" of a patient for cancer screening is intended to be widely construed and includes retrieving, capturing, acquiring, or otherwise obtaining video image frames.

"Analyzing the thermographic image" means to identify a plurality of points (PN) in the image.

A "software interface tool" is a composite of functionality for tumor detection and/or tumor classification using a plurality of user-selectable objects displayed on a display device such as a touchscreen display. One embodiment of a software interface tool which implements a tumor detection method is disclosed in commonly owned and co-pending U.S. patent application Ser. No. 14/668,178, entitled: "Software Interface Tool For Breast Cancer Screening", by Krithika Venkataramani et al. Another embodiment of a software interface tool which implements a tumor classification method is disclosed in commonly owned and co-pending U.S. patent application Ser. No. 15/053,767, entitled: "Software Interface Tool For Breast Cancer Screening", by Gayatri Sivakumar et al. Various embodiments of the software interface tool perform manual, semi-automatic, and automatic selection of a block of pixels in the thermal image for screening.

FIG. 1 illustrates an example female patient 100 with a thermal imaging camera mounted on a slidable and axially rotatable robotic arm for moving the thermal camera along a semi-circular trajectory from side-to-side in front of the patient according to an embodiment herein. The thermal imaging camera 101 is mounted on the slidable and axially rotatable robotic arm 102 capable of moving the thermal imaging camera along a semi-circular trajectory 103 in the front of the patient/subject from side-to-side such that thermographic images may be captured in a right-side view 104, a front view 105, and a left-side view 106, and various oblique angles in between. The thermal imaging camera 101 can be a single-band infrared camera, a multi-band infrared camera in the thermal range and a hyper spectral infrared camera in the thermal range. The resolution of the thermal imaging camera 101 is effectively the size of the pixel. Smaller pixels mean that the resulting image has a higher resolution and thus better spatial definition. Although the thermal imaging camera 101 offers a relatively large dynamic range of temperature settings, it is preferable that the camera's temperature range be relatively small, centered around the person's body surface temperature so that small temperature variations are amplified in terms of pixel color changes in order to provide a better measure of temperature variation. Thermal imaging cameras are readily available in various streams of commerce. The thermal imaging camera 101 is communicatively connected to a corrective positioning system 107 which process the thermal image captured by the thermal imaging camera 101 for identifying errors associated with subject positioning in a thermal image from a user/robotic arm and generating a feedback to enable the user for adaptive positioning of the subject for capturing a new thermal image.

Figure 2A:
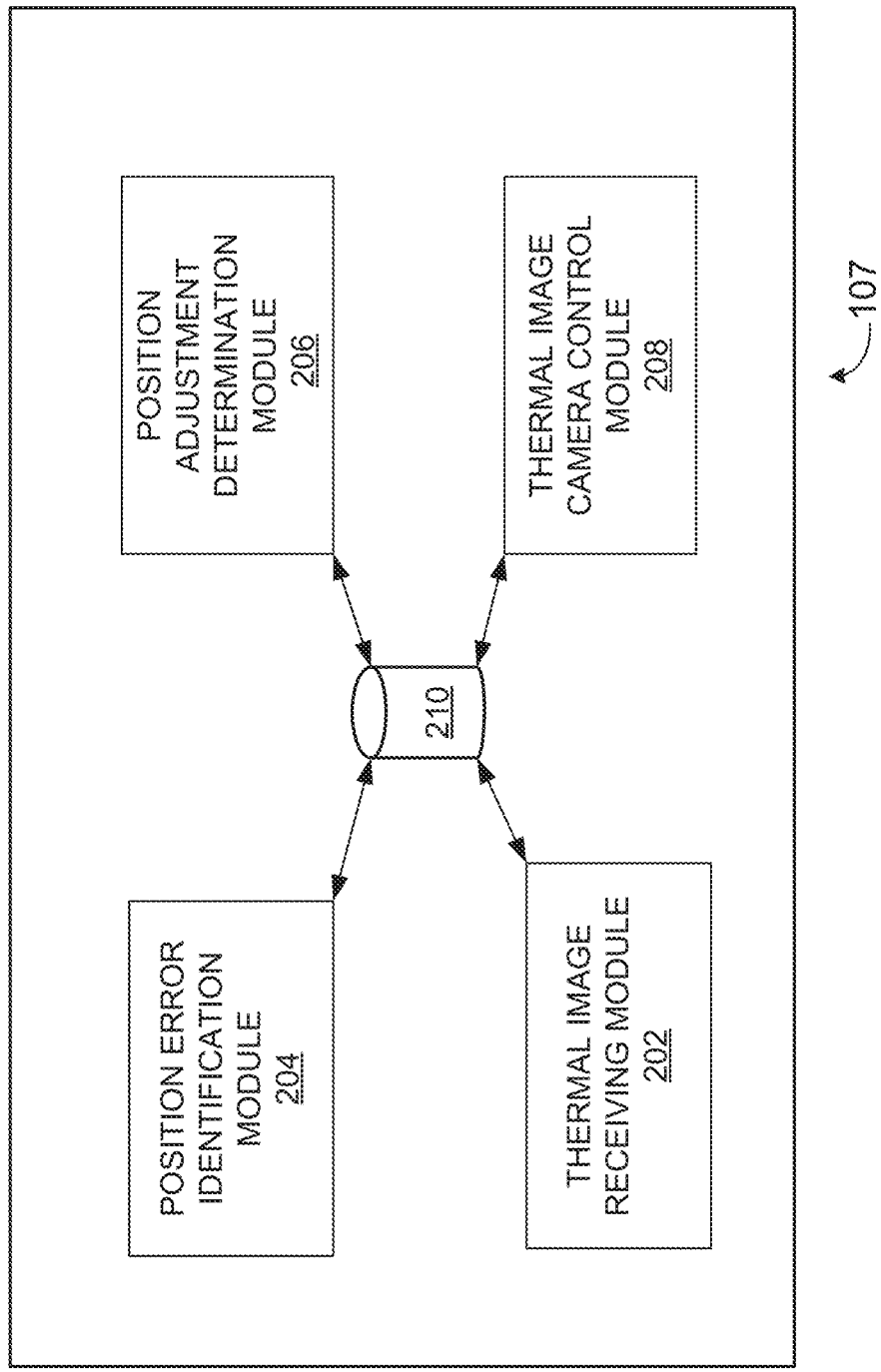
FIG. 2A illustrates an exploded view of a corrective positioning system for identifying errors associated with a subject positioning in a thermal image of the subject from a user and determining, applying a positional adjustment for adaptive positioning of the subject for capturing a new thermal image according to an embodiment herein.

FIG. 2A illustrates an exploded view of a corrective positioning system for identifying errors associated with a subject positioning in a thermal image of the subject from a user and determining, applying a positional adjustment for adaptive positioning of the subject for capturing a new adjusted thermal image according to an embodiment herein. The corrective positioning system 107 includes a thermal image receiving module 202, a position error identification module 204, a position adjustment determination module 206 and a thermal image camera control module 208. The thermal image receiving module 202 receives an initial thermal image of a body of a subject/patient. The initial thermal image represents the temperature distribution on the body of the subject as pixels in the initial thermal image with a highest temperature value being displayed in a first color and pixels with a lowest temperature value being displayed in a second color, pixels with temperature values between the lowest and highest temperature values being displayed in gradations of color between the first and second color. In an embodiment, the initial thermal image is captured using a thermal imaging camera which is connected with the corrective positioning system 107. In an embodiment, the thermal imaging camera includes an array of sensors, a lens and a specialized processor. The array of sensors converts an infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the initial thermal image. The position error identification module 204 automatically identifies errors associated with the subject positioning in the initial thermal image. In an embodiment, the position adjustment includes (i) adjusting at least one of the thermal imaging camera, or the subject chair up or down to capture a new adjusted thermal image to obtain visible region above the breast region (p) and a part of visible region below the breast region (q) is as per thermal imaging protocol; (ii) adjusting at least one of the thermal imaging camera, the subject or the subject chair front/back to capture the new adjusted thermal image to obtain visible region above the breast region (p) and the part of visible region below the breast region (q) is as per the thermal imaging protocol; and (iii) adjusting at least one of the thermal imaging camera, the subject or the subject chair sideways with the distance of the breast region from either of the first or the last pixel column (r) is as per the thermal imaging protocol.

In an embodiment, the thermal imaging protocol includes at least one steps of (i) cooling the initial thermal image for a particular time interval, (ii) positioning the subject in such a way that the initial thermal image of the complete chest area with axilla is visible, (iii) focusing the initial thermal image of the subject for capturing the high-resolution initial thermal image of the subject, (iv) capturing the initial thermal image of the subject in at least one of front view, left oblique view, left lateral view, right oblique view or right lateral view or (v) providing the initial thermal image of the subject to the system for further analysis. The position error identification module 204 automatically computes a plurality of positions (p,q,r) of the breast region with respect to the initial thermal image. The position p is the normalized distance from the top of the initial thermal image to the upper end of the breast region, the position q is the normalized distance from the lower end of breast to the end/bottom of the initial thermal image and the position r is the normalized distance of side boundary of breast (close to sternum) to the first or last pixel column of the initial thermal image. The position error identification module 204 computes a plurality of deviations (dp, dq, dr) in the plurality of positions of the breast region by comparing the plurality of positions of the breast region with a required position as per the thermal imaging protocol. The deviation dp is a deviation with respect to visible region above the breast region in the initial thermal image, the deviation dq is a deviation with respect to visible region below the breast region in the initial thermal image and the deviation dr is a deviation with respect to the distance of the breast region from either the first or the last pixel column of the initial thermal image. In an embodiment, the position error identification module 204 computes a plurality of positions (p,q,r) of the breast region with respect to the initial thermal image that is obtained by selecting a single image frame of a thermal video or a live stream thermal video. In an embodiment, the values of positions p,q,r of the breast region for a typical thermal imaging protocol can be predefined for different views. For example, the predetermined value is 15% of the thermal image height for frontal, lateral and oblique views for the visible region above the breast region in the initial thermal image (p). The predetermined value for the visible region below the breast region in the initial thermal image (q) is 15% of the initial thermal image height for frontal, lateral and oblique views. The predetermined value for the distance of the breast region from either the first or the last pixel column of the initial thermal image (r) is 50% of image width for frontal and lateral views and 67.78% of image width for the oblique view.

The position adjustment determination module 206 determines a positional adjustment to be made to a view position of the thermal imaging camera or a position of the subject based on the plurality of deviations (dp, dq, dr) in the plurality of positions of the breast region using a machine learning model. The thermal image camera control module 208 provides set of instructions to technician or at least one of a robotic arm holding the camera, an electronically controlled camera stand or an electronically controlled rotating chair to automatically position itself to the suggested angular adjustment for capturing the new adjusted thermal image at the required view angle as per thermal image protocol. The set of instructions includes at least one of a text, a visual or audio for capturing the new adjusted thermal image at the required view angle. In an embodiment, the corrective positioning system 107 provides the new adjusted thermal image along with corrective position adjustment for an automatic tumor detection and an automated tumor classification to detect cancerous tissue and/or non-cancerous tissue within a breast area of the subject using a thermal image analyzer. In an embodiment, the positional adjustment is provided to automatically adjust the position of the thermal imaging camera to capture the new thermal image at the required position without the user's intervention.

In an embodiment, the corrective positioning system 107 adapted with a segmentation system or module that implements an automatic segmenting technique to segment the breast area of the subject in the initial thermal image to predict a segmentation map on the thermal image. The automatic segmenting technique predicts the segmentation map on the initial thermal image by determining (i) an outer side contour of an outline of a boundary of the breast area of the subject from a body silhouette, (ii) an inner side boundary of the breast area from the body silhouette and the view angle of the initial thermal image, (iii) an upper boundary of the breast area by determining a lower boundary of an isotherm of axilla of the subject, or (iv) a lower boundary of the breast area by determining an upper boundary of an isotherm of infra-mammary fold of the person. The adaptive view angle positioning system 107 segments the breast area of the subject by connecting above determined breast boundaries to segment the breast from surrounding tissue in the initial thermal image. In an embodiment, the corrective positioning system 107 may include a machine learning model for automatically segmenting the breast area of the subject in the initial thermal image. The machine learning model is trained by providing a plurality of thermal images as an input and the corresponding segmentation as an output to obtain a trained deep learning model.

The corrective positioning system 107 provides the new adjusted thermal image to the trained deep learning model to predict the segmentation map. In some embodiments, the segmentation map includes the plurality of positions (p, q, r). The corrective positioning system 107 may display at least one of the positional adjustment or the segmented breast region on a visualization screen. In an embodiment, the automatic tumor detection includes the steps of (i) determining a percentage of pixels $p_1$ within said selected region of interest with a temperature $T^1_{pixel}$, where $T_2 \leq T^1_{pixel} \leq T_1$, (ii) determining a percentage of pixels $p_2$ within said selected region of interest with a temperature $T^2_{pixel}$, where $T_3 \leq T^2_{pixel}$ and (iii) determining a ratio $p_3 = P_{edge}/P_{block}$, where $P_{edge}$ is a number of pixels around a border of a suspected tumor within said region of interest, and $P_{block}$ is a number of pixels in the perimeter of the region of interest. The $T_1$, $T_2$ and $T_3$ are temperature threshold obtained from temperature distribution. The automatic tumor detection includes determining whether a suspected tumor region as one of: the cancerous tissue, the non-cancerous using a decision rule R. The decision rule R is based on any combination of: $R_1$, $R_2$, $R_3$, where: $R_1=(p_1>Threshold_1)$, $R_2=(p_2>Threshold_2)$, and $R_3=(p_3>Threshold_3)$. In an embodiment, the automatic tumor classification includes the steps of: (i) determining pixel regions $m_1$ within a selected region of interest with a temperature $T^1_{pixel}$, where $T_2 \leq T^1_{pixel} \leq T_1$; (ii) determining pixel regions $m_2$ within the selected region of interest with a temperature $T^2_{pixel}$, where $T_3 \leq T^2_{pixel}$; (iii) extracting the parameters comprising at least one temperature, at least one boundary, at least one area and at least one shape from $m_1$ and $m_2$; and (iv) providing the parameters to a machine learning classifier to determine whether the selected region of interest has a cancerous lesion or not. $T_1$, $T_2$ and $T_3$ are temperature thresholds obtained from temperature distribution. The automatic tumor classification includes the steps of: (i) training a deep learning model by providing a plurality of thermal images as an input and the corresponding classification as an output to obtain a trained deep learning model; and (ii) providing the new adjusted thermal image to the trained deep learning model to determine whether a selected region of interest has a cancerous lesion or not.

With reference to FIG. 2A, FIG. 2B-2E illustrate exemplary thermal images processed by an automated segmentation technique to determine a breast region in the thermal images of a subject according to an embodiment herein. The thermal images are captured by a thermal imaging camera. The captured thermal images may include errors in a position of the subject. In some embodiments, in the captured thermal images shown in 2B, 2C and 2D, the subject is positioned far 212, close 214 or not centered 216, which is considered to be the errors. In some embodiments, the position error identification module 204 identifies the errors in the position of the subject in a thermal image. The automatic segmentation technique includes a deep learning model that segments the thermal images to predict a final segmentation map. The final segmentation map includes the plurality of positions p, q, r as shown in FIG. 2E. In some embodiments, the position p represents a thorax region 218, q represents abdomen region 220 and r represents sternum region 222. In some embodiments, the position error identification module 204 automatically computes the plurality of positions (p, q, r) of the breast region with respect to the thermal image. For example, the predetermined value is 15% of the thermal image height for frontal, lateral and oblique views for the thorax region (p) 218 in the thermal image. The predetermined value for the abdomen region (q) 220 is 15% of the thermal image height for frontal, lateral and oblique views. The predetermined value for the sternum region (r) 222 is 50% of image width for frontal and lateral views and 67.78% of image width for the oblique view. In some embodiments, the thorax region (p) 218 is a normalized length of visible region above the breast region in the thermal image, the abdomen region (q) 220 is a normalized length of visible region below the breast region in thermal image and the sternum region (r) 222 is a distance of the breast region from either of a first or a last pixel column of the thermal image.

With reference to FIG. 1, FIG. 3 illustrates an exemplary process flow of the automated Region of Interest (ROI) analysis of a thermal image from a user using a corrective positioning system according to an embodiment herein. At step 302, the thermal image is captured using a thermal imaging camera. In some embodiments, the thermal image may be received or retrieved from a remote device over a network, or from a media such as a CDROM or DVD. The thermal image may be downloaded from a web-based system or an application that makes a video available for processing in accordance with the methods disclosed herein. The thermal image may also be received from an application such as those which are available for handheld cellular devices and processed on the cell phone or other handheld computing devices such as an iPad or Tablet-PC. The thermal image may be received directly from a memory or storage device of the imaging device that is used to capture that thermal image or a thermal video. At step 304, the thermal image is obtained by selecting a single image frame of a thermal video or a live stream thermal video. The thermal video or the live stream thermal video is captured using the thermal imaging camera. At step 306, the breast region in the thermal image is segmented from the thermal image using an automated segmentation technique. At step 308, the segmented breast region is provided for further analysis (e.g. breast cancer screening and tumor classification).

Figure 4:
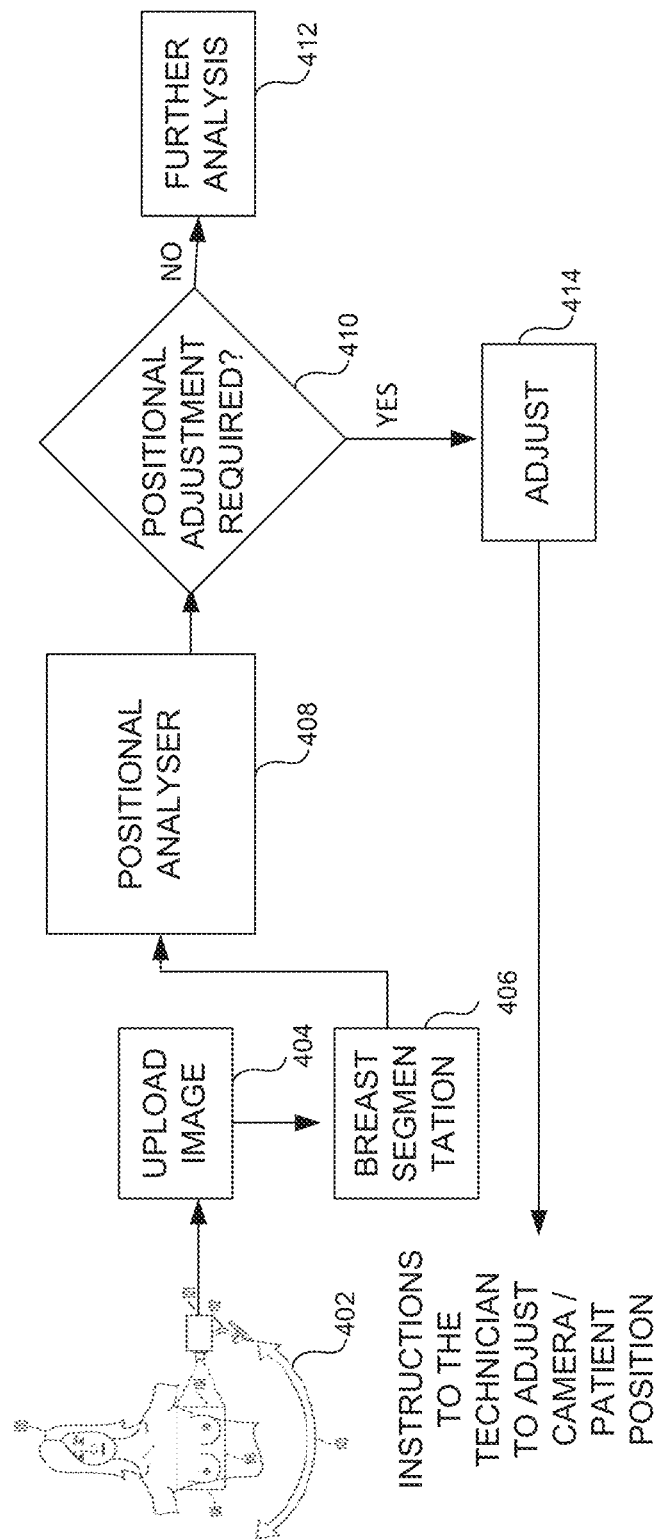
FIG. 4 illustrates an exemplary process flow of an offline error identification associated with subject positioning in a thermal image from a user and generating a feedback to enable the user for adaptive positioning of the subject for capturing a new thermal image using a corrective positioning system according to an embodiment herein.

With reference to FIG. 1, FIG. 4 illustrates an exemplary process flow of an offline positional adjustment for a thermal image from a user using a corrective positioning system according to an embodiment herein. At step 402, the thermal image is captured using a thermal imaging camera. At step 404, the thermal image is uploaded into the corrective positioning system. At step 406, the breast region is segmented from the thermal image using an automated segmentation technique. In some embodiments, the automated segmentation technique predicts a final segmentation map on the thermal image. At step 408, the corrective positioning system computes a plurality of positions (p,q,r) of the breast region with respect to the thermal image with the final segmentation map and a plurality of deviations (dp, dq, dr) in the plurality of positions of the breast region by comparing the plurality of positions of the breast region with a required position as per the thermal imaging protocol using a position analyzer. The position p is the normalized distance from the top of the thermal image to the upper end of the breast region, the position q is the normalized distance from the lower end of breast to the end/bottom of the thermal image and the position r is the normalized distance of side boundary of breast (close to sternum) to the first or last pixel column of the thermal image. The deviation dp is a deviation with respect to visible region above the breast region in the thermal image, the deviation dq is a deviation with respect to visible region below the breast region in the thermal image and the deviation dr is a deviation with respect to the distance of the breast region from either the first or the last pixel column of the thermal image. At step 410, it is determined whether a positional adjustment to be made to a position of thermal imaging camera or a position of the subject based on the plurality of deviations (dp, dq, dr) in the plurality of positions of the breast region using a machine learning model. At step 412, the thermal image is provided for further analysis, for example, breast cancer screening or tumor classification, if the thermal image is captured at the required position as per the thermal imaging protocol. If not, at step 414, a set of instructions to the user is generated for adjusting a position of the thermal imaging camera or subject for capturing a new thermal image at the required position as per thermal imaging protocol.

Figure 5:
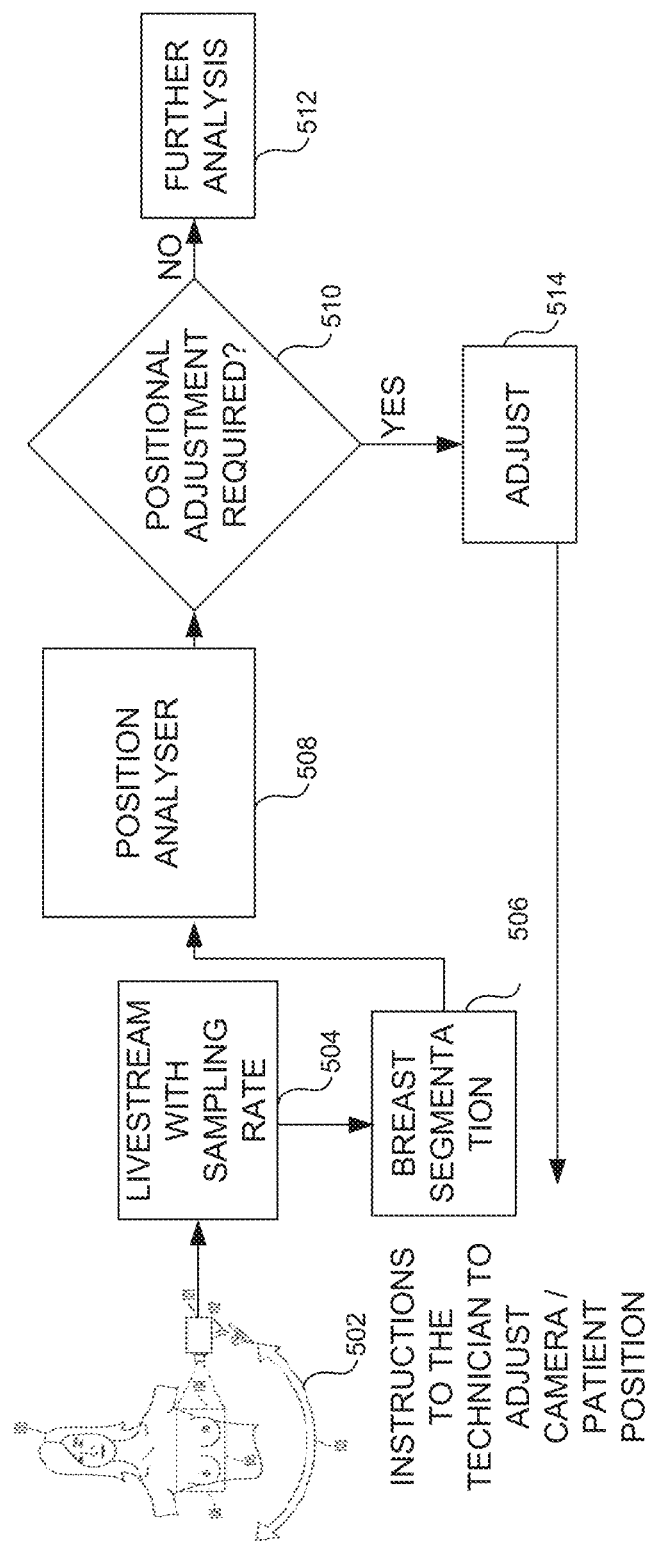
FIG. 5 illustrates an exemplary process flow of a live stream error identification associated with subject positioning in a thermal image from a user and generating a feedback to enable the user for adaptive positioning of the subject for capturing a new thermal image using a corrective positioning system according to an embodiment herein.

With reference to FIG. 1, FIG. 5 illustrates an exemplary process flow of a live stream positional adjustment for a thermal image from a user using a corrective positioning system according to an embodiment herein. At step 502, the live stream with sequential frames (e.g. thermal image/video) is captured using a thermal imaging camera. At step 504, a sample rate or adaptive sampling algorithms are applied to analyze selected frames of the thermal video instead of all frames to determine the corrective position for capturing a thermal image. At step 506, the breast region is segmented from the thermal image using an automated segmentation technique. In some embodiments, the automated segmentation technique predicts a final segmentation map on the thermal image. At step 508, the corrective positioning system computes a plurality of positions (p,q,r) of the breast region with respect to the thermal image with the final segmentation map and a plurality of deviations (dp, dq, dr) in the plurality of positions of the breast region by comparing the plurality of positions of the breast region with a required position as per the thermal imaging protocol using a position analyzer. The position p is the normalized distance from the top of the thermal image to the upper end of the breast region, the position q is the normalized distance from the lower end of breast to the end/bottom of the thermal image and the position r is the normalized distance of side boundary of breast (close to sternum) to the first or last pixel column of the thermal image. The deviation dp is a deviation with respect to visible region above the breast region in the thermal image, the deviation dq is a deviation with respect to visible region below the breast region in the thermal image and the deviation dr is a deviation with respect to the distance of the breast region from either the first or the last pixel column of the thermal image. At step 510, it is determined whether a positional adjustment to be made to a position of thermal imaging camera or a position of the subject based on the plurality of deviations (dp, dq, dr) in the plurality of positions of the breast region using a machine learning model. At step 512, the thermal image is provided for further analysis, for example, breast cancer screening or tumor classification, if the thermal image is captured at the required position as per the thermal imaging protocol. If not, at step 514, a set of instructions to the user is generated for a position of the thermal imaging camera or subject for capturing a new thermal image at the required position as per thermal imaging protocol.

Figure 6:
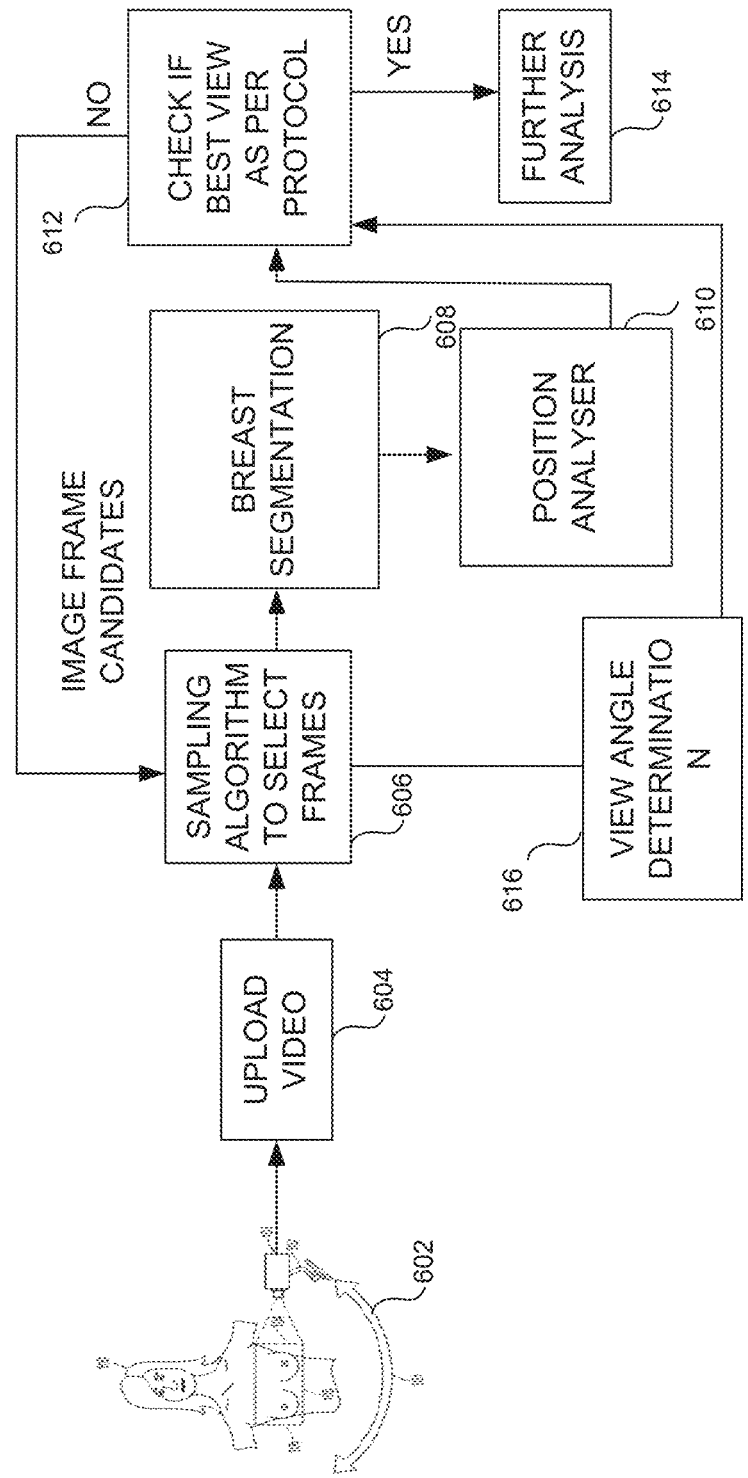
FIG. 6 illustrates an exemplary process flow of corrective positioning using a corrective positioning system to select a view with adaptive sampling to reduce image frame candidates according to an embodiment herein.

With reference to FIG. 1, FIG. 6 illustrates an exemplary process flow of corrective positioning using a corrective positioning system to select a view with adaptive sampling to reduce image frame candidates according to an embodiment herein. At step 602, the thermal video is captured using a thermal imaging camera. At step 604, the thermal video is uploaded to the corrective positioning system. At step 606, a sample rate or adaptive sampling algorithms are applied to analyze the thermal video to select frames of the thermal video for each desired view angle (e.g. 45°, 90°, −45°, −90°, 0°) which has less deviation with angle and position instead of all frames to determine the corrective position. At step 608, the breast region is segmented from the selected frame using an automated segmentation technique. In some embodiments, the automated segmentation technique predicts a final segmentation map on the thermal image. At step 610, the corrective positioning system computes a plurality of positions (p,q,r) of the breast region with respect to the thermal image with the final segmentation map and a plurality of deviations (dp, dq, dr) in the plurality of positions of the breast region by comparing the plurality of positions of the breast region with a required position as per the thermal imaging protocol using a position analyser and determines positional adjustment to be made to a position of thermal imaging camera or a position of the subject based on the plurality of deviations (dp, dq, dr) in the plurality of positions of the breast region using a machine learning model. The position p is the normalized distance from the top of the thermal image to the upper end of the breast region, the position q is the normalized distance from the lower end of breast to the end/bottom of the thermal image and the position r is the normalized distance of side boundary of breast (close to sternum) to the first or last pixel column of the thermal image.

The deviation dp is a deviation with respect to visible region above the breast region in the thermal image, the deviation dq is a deviation with respect to visible region below the breast region in the thermal image and the deviation dr is a deviation with respect to the distance of the breast region from either the first or the last pixel column of the thermal image. At step 612, the view angle of the selected frame of the thermal image is determined using a tagging classifier. The tagging classifier includes a machine learning model that determines the view angle of the thermal image and classifies the thermal image as one of the discrete views such as a right lateral view, a right oblique view, a frontal view, a left lateral view or a left oblique view as per the thermal imaging protocol. At step 614, it is determined the thermal frame which meets the requirement of the thermal imaging protocol by (i) comparing the determined positions with the required positions as per thermal imaging protocol and (ii) comparing the determined view angle with the required view angle as per thermal imaging protocol. At step 616, the determined thermal frames are provided for further analysis, for breast cancer screening or tumor detection, if the thermal frames areas per the thermal imaging protocol. If not, it goes back to step 606 to adjust the sampling rate.

In an embodiment, the required thermal frames selected from a captured thermal video of a subject (e.g. frames to be considered 0, ±45, ±90) are used for automated analysis. The input to the corrective positioning system is the entire frames from the thermal video or sampled frame from any adaptive sampling algorithm. The corrective positioning system determines the best frames corresponding to the required position of capturing a thermal image.

In an embodiment, the frame selection from the thermal video includes determining a view angle of the thermal image from a user using a view angle estimator. It includes determining an angular adjustment to be made to a view position of the thermal imaging camera or a position of the subject by comparing the determined view angle with a required view angle as per thermal imaging protocol when the thermal image does not meet the required view angle.

Figure 7:
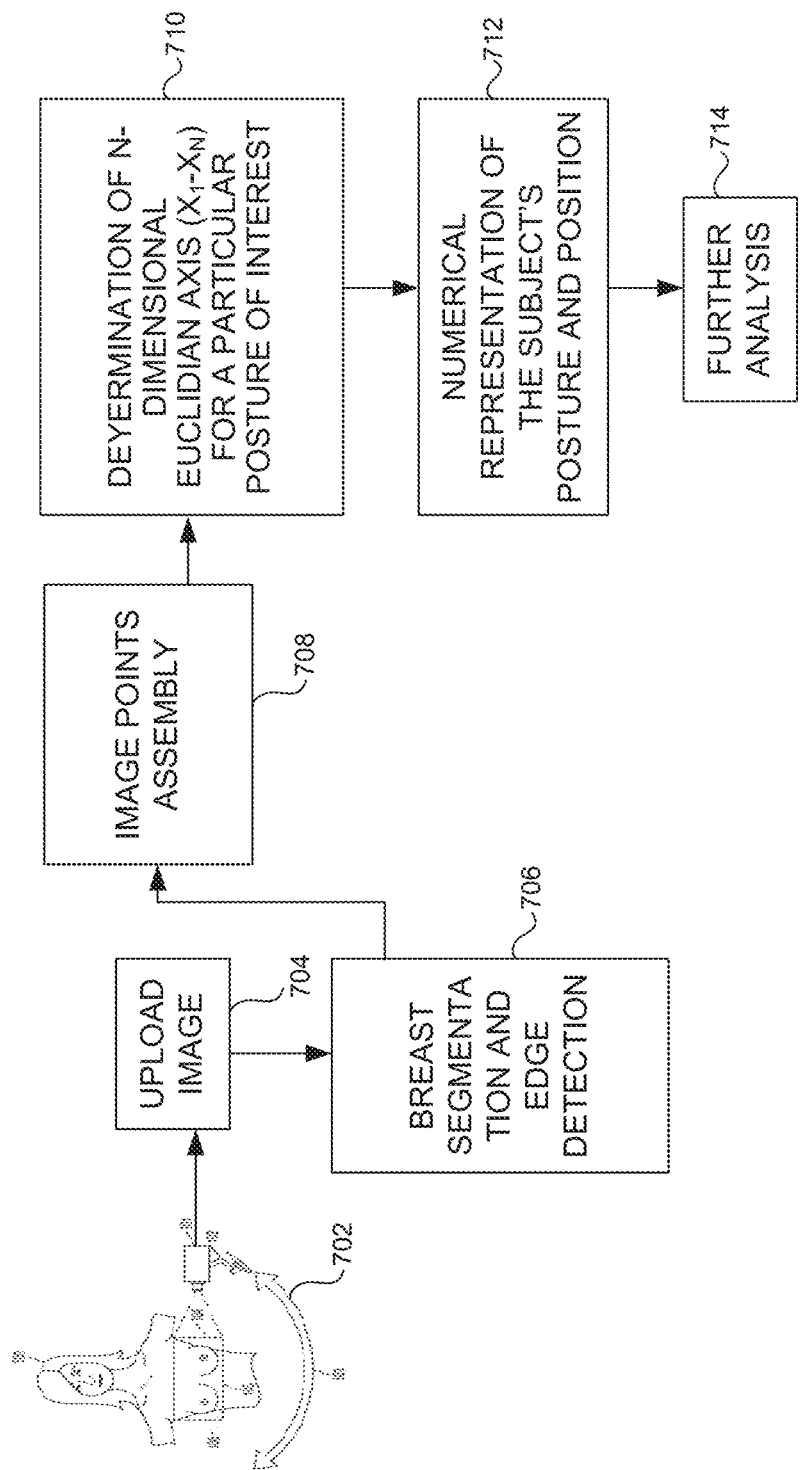
FIG. 7 illustrates an exemplary process flow of automatically identifying a posture and a position of a subject in a thermal image according to an embodiment herein.

With reference to FIG. 1, FIG. 7 illustrates an exemplary process flow of automatically identifying a posture and a position of a subject in a thermal image according to an embodiment herein. At step 702, the thermal image is captured using a thermal imaging camera. At step 704, the thermal image is uploaded into a posture and a position identification system. At step 706, key physical structures and contours of the body in the thermal image is determined using an automated segmentation technique and an edge detection technique and represented as image points to define a reference body coordinate system in an n-dimensional Euclidean space. At step 708, the posture and a position identification system assemble each image point in the Euclidean coordinate system to define the posture and the position of the body. At step 710, the n-dimensional Euclidian axis (X1-Xn) for a particular posture of interest is determined to define the reference body coordinate system. Each Euclidian axis includes values associated with a physical structure or contour of the body. The values of each Euclidian axis (Xi=1–N) represents a relative distance of the respective physical structure or contour of the body from the boundaries of the thermal image. At step 712, N ordinal values along each corresponding n-dimensional Euclidian axis for the given image is provided as a numerical representation of the subject's posture, position and a point in a Euclidian space to enable the user to perform further analysis, for example, breast cancer screening or tumor classification.

Figure 8A:
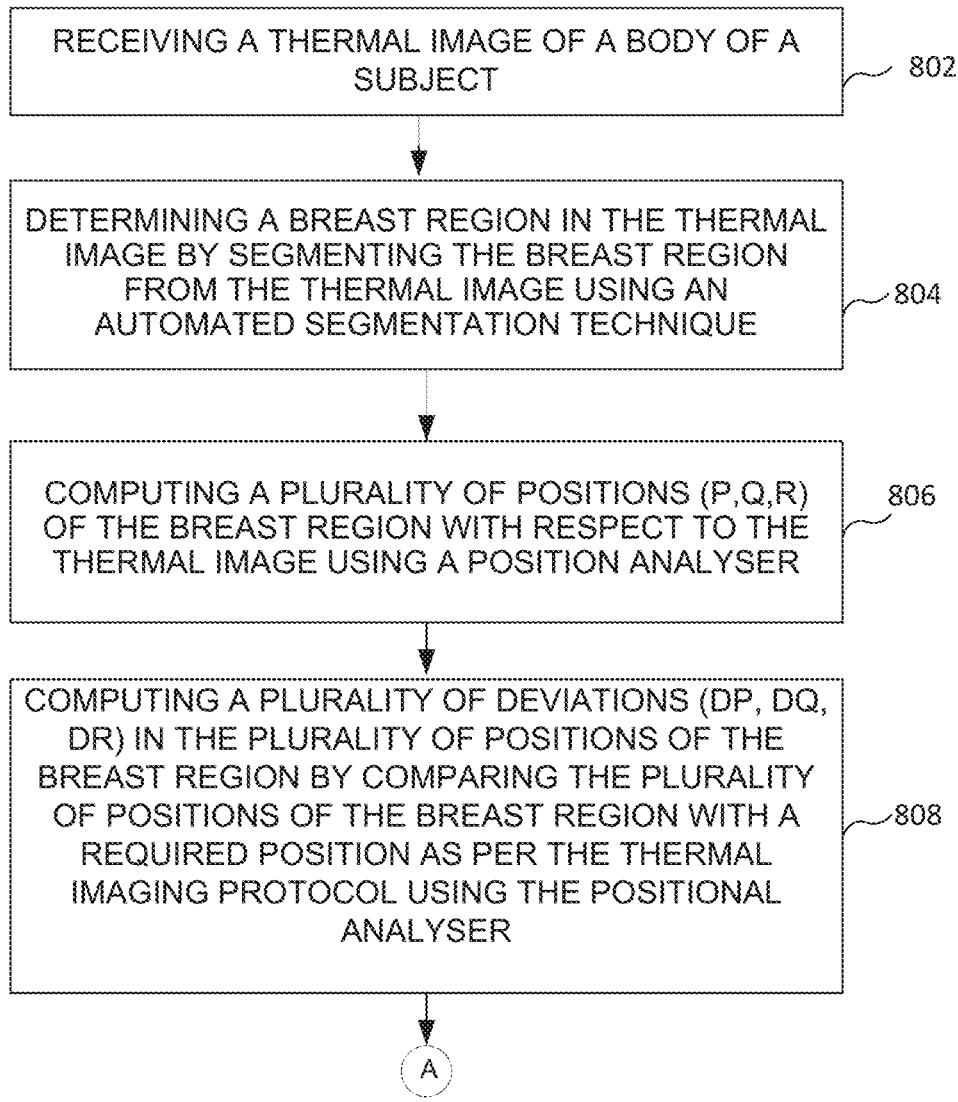
FIGS. 8A and 8B illustrate a flow diagram of one embodiment of the present method for identifying errors associated with subject positioning in a thermal image from a user and generating a feedback to enable the user for adaptive positioning of the subject for capturing a new thermal image according to an embodiment herein.
Figure 8B:
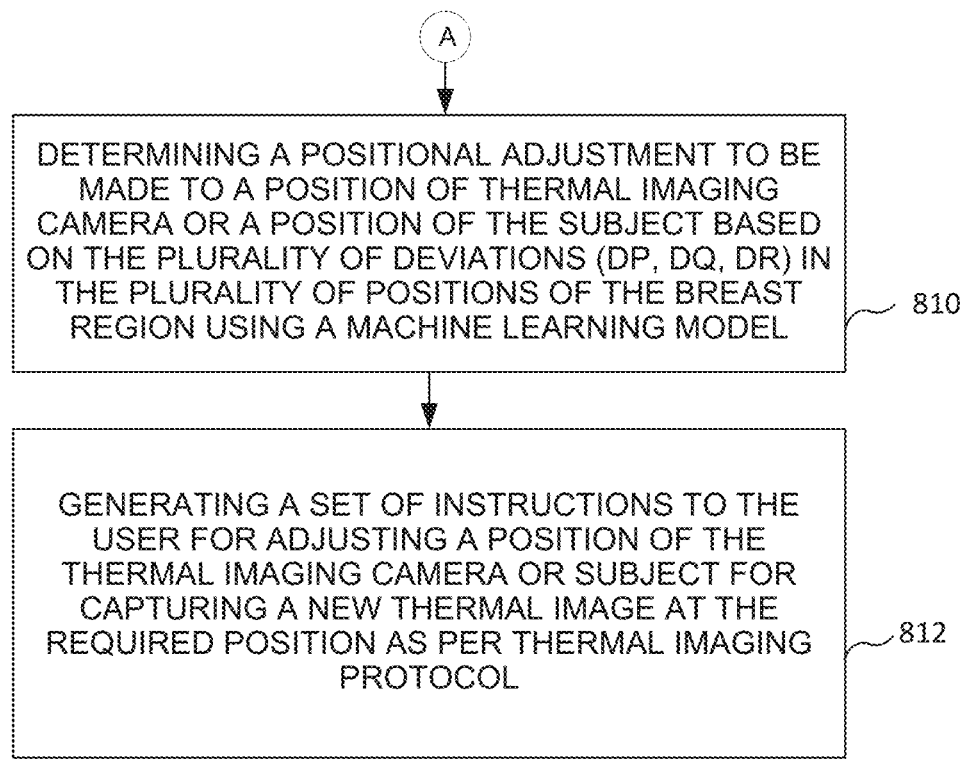

FIGS. 8A and 8B illustrate a flow diagram of one embodiment of the present method for identifying errors associated with subject positioning in a thermal image from a user and generating a feedback to enable the user for adaptive positioning of the subject for capturing a new thermal image, according to an embodiment herein. At step 802, a thermal image of a body of a subject is received. The thermal image represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second colors. At step 804, a breast region in the thermal image is determined by segmenting the breast region from the thermal image using an automated segmentation technique. At step 806, a plurality of positions (p,q,r) of the breast region with respect to the thermal image is computed using a position analyzer. The position p is the normalized distance from the top of the thermal image to the upper end of the breast region, the position q is the normalized distance from the lower end of breast to the end/bottom of the thermal image and the position r is the normalized distance of side boundary of breast (close to sternum) to the first or last pixel column of the thermal image. At step 808, a plurality of deviations (dp, dq, dr) in the plurality of positions of the breast region is computed by comparing the plurality of positions of the breast region with a required position as per the thermal imaging protocol by using the position analyzer. The deviation dp is a deviation with respect to visible region above the breast region in the thermal image, the deviation dq is a deviation with respect to visible region below the breast region in the thermal image and the deviation dr is a deviation with respect to the distance of the breast region from either the first or the last pixel column of the thermal image. At step 810, a positional adjustment to be made to a position of thermal imaging camera or a position of the subject is determined based on the plurality of deviations (dp, dq, dr) in the plurality of positions of the breast region using a machine learning model. At step 812, a set of instructions is generated to the user for adjusting a position of the thermal imaging camera or subject for capturing a new thermal image at the required position as per thermal imaging protocol.

Figure 9:
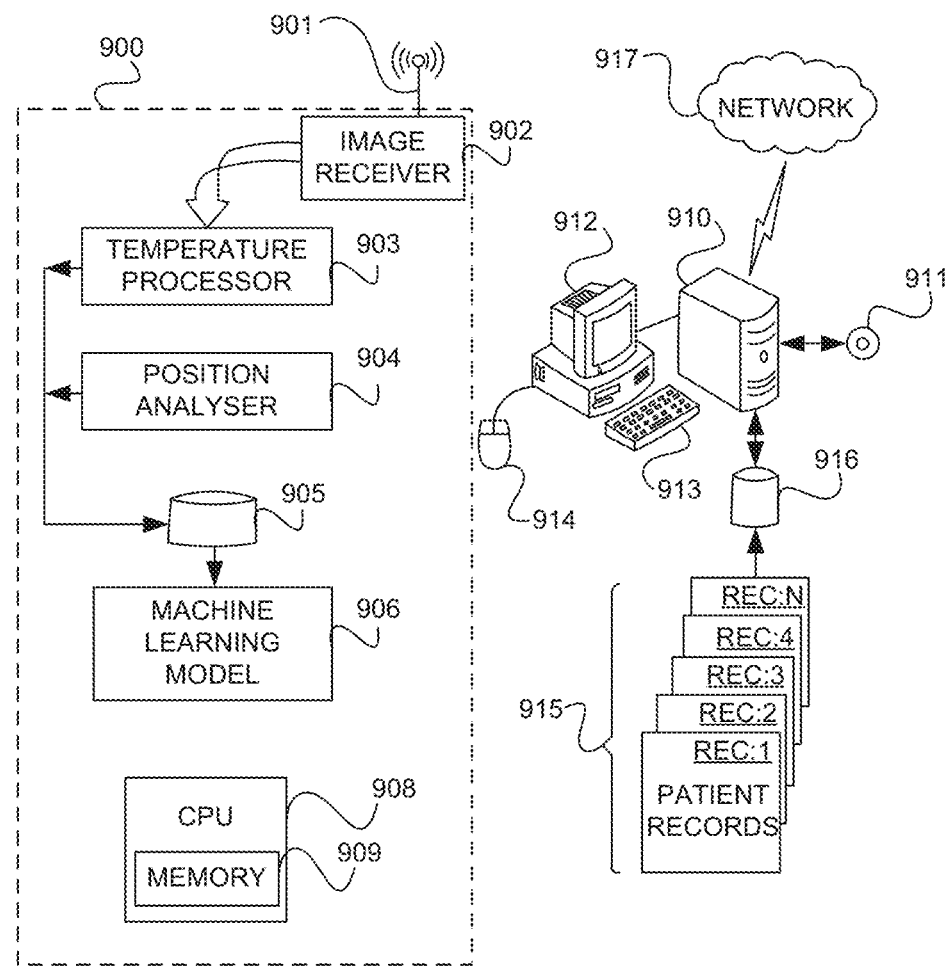
FIG. 9 illustrates a block diagram of one example corrective positioning system/image processing system for processing a thermal image in accordance with the embodiments described with respect to the flow diagram of FIGS. 8A and 8B according to an embodiment herein.

FIG. 9 illustrates a block diagram of one example of corrective positioning system/image processing system 900 for processing a thermal image in accordance with the embodiments described with respect to the flow diagram of FIGS. 8A and 8B according to an embodiment herein. Image Receiver 902 wirelessly receives the video via antenna 901 having been transmitted thereto from the video/thermal imaging device 101 of FIG. 1. Temperate Processor 903 performs a temperature-based method to detect pixels in the received image. Position analyzer904 computes a plurality of positions (p,q,r) of the breast region with respect to the thermal image and a plurality of deviations (dp, dq, dr) in the plurality of positions of the breast region is computed by comparing the plurality of positions of the breast region with a required position as per the thermal imaging protocol. The position p is the normalized distance from the top of the thermal image to the upper end of the breast region, the position q is the normalized distance from the lower end of breast to the end/bottom of the thermal image and the position r is the normalized distance of side boundary of breast (close to sternum) to the first or last pixel column of the thermal image. The deviation dp is a deviation with respect to visible region above the breast region in the thermal image, the deviation dq is a deviation with respect to visible region below the breast region in the thermal image and the deviation dr is a deviation with respect to the distance of the breast region from either the first or the last pixel column of the thermal image. Both Modules 903 and 904 store their results to storage device 905. Machine learning mode1906 retrieves the results from the storage device 905 and proceeds to a positional adjustment to be made to a position of thermal imaging camera 101 or a position of the subject based on the plurality of deviations (dp, dq, dr) in the plurality of positions of the breast region. when the thermal image does not meet the required position for image capture as per thermal imaging protocol, the machine learning model 906 generates a set of instructions to the user for adjusting the position of the thermal imaging camera 101 for capturing the new thermal image at the required position as per thermal imaging protocol. Central Processing Unit 908 retrieves machine-readable program instructions from a memory 909 and is provided to facilitate the functionality of any of the modules of the system 900. CPU 908, operating alone or in conjunction with other processors, may be configured to assist or otherwise perform the functionality of any of the modules or processing units of the system 900 as well as facilitating communication between the system 900 and the workstation 910.

System 900 is shown having been placed in communication with a workstation 910. A computer case of the workstation houses various components such as a motherboard with a processor and memory, a network card, a video card, a hard drive capable of reading/writing to machine-readable media 911 such as a floppy disk, optical disk, CD-ROM, DVD, magnetic tape, and the like, and other software and hardware needed to perform the functionality of a computer workstation. The workstation further includes a display device 912, such as a CRT, LCD, or touch screen device, for displaying information, images, view angles, and the like. A user can view any of that information and make a selection from menu options displayed thereon. Keyboard 913 and mouse 914 effectuate a user input. It should be appreciated that the workstation has an operating system and other specialized software configured to display alphanumeric values, menus, scroll bars, dials, slidable bars, pull-down options, selectable buttons, and the like, for entering, selecting, modifying, and accepting information needed for processing in accordance with the teachings hereof. The workstation is further enabled to display thermal images, position adjustments to thermal images and the like as they are derived. A user or technician may use the user interface of the workstation to set parameters, view/adjust the position, and adjust various aspects of the position adjustment is performed, as needed or as desired, depending on the implementation. Any of these selections or inputs may be stored/retrieved to storage device 911. Default settings can be retrieved from the storage device. A user of the workstation is also able to view or manipulate any of the data in the patient records, collectively at 915, stored in database 916. Any of the received images, results, determined view angle, and the like, may be stored to a storage device internal to the workstation 910. Although shown as a desktop computer, the workstation can be a laptop, mainframe, or a special purpose computer such as an ASIC, circuit, or the like.

Any of the components of the workstation may be placed in communication with any of the modules and processing units of system 900. Any of the modules of the system 900 can be placed in communication with storage devices 905, 916 and 106 and/or computer-readable media 911 and may store/retrieve therefrom data, variables, records, parameters, functions, and/or machine-readable/executable program instructions, as needed to perform their intended functions. Each of the modules of the system 900 may be placed in communication with one or more remote devices over network 917. It should be appreciated that some or all of the functionality performed by any of the modules or processing units of the system 900 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

What is claimed is:

1. A method for identifying errors associated with a subject positioning in a thermal image of a body of the subject and determining a positional adjustment that is applied for adaptive positioning of the subject for capturing a new adjusted thermal image, the method comprising:
    receiving the thermal image of the body of the subject, which represents a temperature distribution on the body of the subject with a highest temperature value that is displayed in a first color as first pixels and with a lowest temperature value that is displayed in a second color as second pixels, with temperature values between the lowest and highest temperature values that is displayed in gradations of color between the first color and second color as third pixels, wherein the thermal image is captured by a thermal imaging camera, the thermal imaging camera comprising:
        an array of sensors configured to convert an infrared energy into electrical signals on a per-pixel basis;
        a lens configured to focus the infrared energy from the body of the subject onto the array of sensors, wherein the array of sensors detects the highest temperature value, the lowest temperature value, and the temperature values between the lowest and highest temperature values from the body of the subject; and
        a camera processor configured to process the highest temperature value, the lowest temperature value, and the temperature values between the lowest and highest temperature values that are detected into at least one block of pixels to generate the thermal image;
    automatically determining a breast region in the thermal image by segmenting the breast region from the thermal image using an automated segmentation technique, wherein the automated segmentation technique segments the thermal image of the body of the subject to generate a segmentation map within the thermal image;
    computing a plurality of positions comprising a position p, a position q, and a position r of the breast region with respect to the thermal image with the segmentation map, wherein the position p is a normalized length of a region above the breast region in the thermal image, the position q is a normalized length of the region below the breast region in the thermal image and the position r is a distance of the breast region from either of a first or a last pixel column of the thermal image;
    computing a plurality of deviations comprising a deviation dp, a deviation dq, and a deviation dr in the plurality of positions of the breast region by comparing the plurality of positions of the breast region with a position of the breast region as per thermal imaging protocol, wherein the deviation dp is a deviation with respect to the region above the breast region, the deviation dq is a deviation with respect to the region below the breast region and the deviation dr is a deviation with respect to the distance of the breast region from either the first or the last pixel column of the thermal image;
    determining, using a machine learning model, the positional adjustment to be made to a position of the thermal imaging camera or a position of the subject based on the plurality of deviations in the plurality of positions of the breast region; and
    applying the positional adjustment to the thermal imaging camera or the position of the subject by adjusting the position of the thermal imaging camera or the position of the subject for capturing the new adjusted thermal image at the position of the breast region as per the thermal imaging protocol.

2. The method of claim 1, wherein the positional adjustment comprises at least one of:
    adjusting at least one of the position of the thermal imaging camera, or a position of a subject chair in an upward direction or a downward direction to capture the new adjusted thermal image to obtain the region above the position p of the breast region and the region below the position q of the breast region is as per the thermal imaging protocol;
    adjusting at least one of the position of the thermal imaging camera, the position of the subject or the position of the subject chair in a forward direction or a backward direction to capture the new adjusted thermal image to obtain the region above the position p of the breast region and the region below the position q of the breast region is as per the thermal imaging protocol; and adjusting at least one of the position of the thermal imaging camera, the position of the subject or the position of the subject chair in a left direction or a right direction to capture the new adjusted thermal image to obtain the position r of the distance of the breast region from either of the first or the last pixel column is as per the thermal imaging protocol.

3. The method of claim 1, wherein the automated segmentation technique comprises the step of:

determining an outer side contour of an outline of a boundary of the breast region of the subject from a body silhouette;

determining an inner side boundary of the breast region of the subject from the body silhouette and a view angle of the thermal image;

determining an upper boundary of the breast region of the subject from the body silhouette by determining a lower boundary of an isotherm of axilla of the subject;

determining a lower boundary of the breast region of the subject from the body silhouette by determining an upper boundary of an isotherm of an infra-mammary fold of the subject; and connecting the upper boundary of the breast region and the lower boundary of the breast region that are determined for the segmenting the breast region from the body of the subject from surrounding tissue in the thermal image.

4. The method of claim 3, wherein the automated segmentation technique comprises the steps of:

training a deep learning model by providing a plurality of thermal images as an input and a corresponding segmentation as an output to obtain a trained deep learning model; and providing the new adjusted captured thermal image to the trained deep learning model to generate the segmentation map.

5. The method of claim 1, wherein a set of instructions is provided to at least one of a robotic arm holding the thermal imaging camera, an electronically controlled camera stand, or an electronically controlled rotating chair to automatically position to a suggested position adjustment for capturing the new adjusted thermal image of the body of the subject as per the thermal imaging protocol, wherein the set of instructions are generated by the machine learning model.

6. The method of claim 1, wherein the positional adjustment is configured to automatically adjust the position of the thermal imaging camera to capture the new adjusted thermal image at the position of the breast region without user intervention.

7. The method of claim 1, wherein the method comprises displaying at least one of the positional adjustments or the segmented breast region on a visualization screen.

8. The method of claim 1, wherein the segmenting and the plurality of deviations is computed for the thermal image obtained by selecting a single image frame of a thermal video or a live stream thermal video, wherein the thermal video or live stream thermal video is captured using the thermal imaging camera.

9. The method of claim 1, wherein a set of instructions comprises at least one of a text, a visual, or an audio for capturing the new adjusted thermal image at the position of the breast region as per the thermal imaging protocol.

10. The method of claim 1, wherein the method comprises automatic identification of a posture and the position of the subject in the thermal image by automatically determining physical structures and contours of the body of the subject in the thermal image using the automated segmentation technique and an edge detection technique, wherein the physical structures and the contours of the body of the subject are represented as image points to define a reference body coordinate system in an Euclidean space;

assembling the image points in the Euclidean space to define a posture and the position of the subject;

determining an Euclidian axis for a posture of interest to define the reference body coordinate system, wherein the Euclidian axis includes values associated with the physical structure or contour of the body of the subject, wherein the values of the Euclidian axis represents a distance of the physical structure or the contour of the body of the subject from the boundaries of the thermal image;

providing ordinal values along the Euclidian axis for the thermal image as a numerical representation of the posture of the subject, the position of the subject and the image points in the Euclidean space.

11. A system for identifying errors associated with a subject positioning in a thermal image of a body of the subject and determining a positional adjustment that is applied for adaptive positioning of the subject for capturing a new adjusted thermal image, the system comprising:

a non-transitory storage device; and a processor retrieving machine-readable instructions from the non-transitory storage device which, when executed by the processor, enable the processor to:

receive the thermal image of the body of the subject, which represents a temperature distribution on the body of the subject with a highest temperature value that is displayed in a first color as first pixels and with a lowest temperature value that is displayed in a second color as second pixels, with temperature values between the lowest and highest temperature values that is displayed in gradations of color between the first color and second color as third pixels, wherein the thermal image is captured by a thermal imaging camera, the thermal imaging camera comprising:

an array of sensors configured to convert an infrared energy into electrical signals on a per-pixel basis;

a lens configured to focus the infrared energy from the body of the subject onto the array of sensors, wherein the array of sensors detects the highest temperature value, the lowest temperature value, and the temperature values between the lowest and highest temperature values from the body of the subject; and a camera processor configured to process the highest temperature value, the lowest temperature value, and the temperature values between the lowest and highest temperature values that are detected into at least one block of pixels to generate the thermal image;

automatically determine a breast region in the thermal image by segmenting the breast region from the thermal image using an automated segmentation technique, wherein the automated segmentation technique segments the thermal image of the body of the subject to generate a segmentation map within the thermal image;

compute a plurality of positions comprising a position p, a position q, and a position r of the breast region with respect to the thermal image with the segmentation map, wherein the position p is a normalized length of a region above the breast region in the thermal image, the position q is a normalized length of the region below the breast region in the thermal image and the position r is a distance of the breast region from either of a first or last pixel column of the thermal image;

compute a plurality of deviations comprising a deviation dp, a deviation dq, and a deviation dr in the plurality of positions of the breast region by comparing the plurality of positions of the breast region with to a position of the breast region as per thermal imaging protocol, wherein the deviation dp is a deviation with respect to the region above the breast region, the deviation dq is a deviation with respect to the region below the breast region and the deviation dr is a deviation with respect to the distance of the breast region from either the first or the last pixel column of the thermal image;

determine, using a machine learning model, the positional adjustment to be made to a position of the thermal imaging camera or a position of the subject based on the plurality of deviations in the plurality of positions of the breast region; and apply the positional adjustment to the thermal imaging camera or the position of the subject by adjusting the position of the thermal imaging camera or the position of the subject for capturing the new adjusted thermal image at the position of the breast region as per the thermal imaging protocol.

12. The system of claim 11, wherein the system implements the position adjustment by:

adjust at least one of the position of the thermal imaging camera, or a position of a subject chair in an upward direction or a downward direction to capture the new adjusted thermal image to obtain the region above the position p of the breast region and the region below the position q of the breast region is as per the thermal imaging protocol;

adjust at least one of the position of the thermal imaging camera, the position of the subject or the position of the subject chair in a forward direction or a backward direction to capture the new adjusted thermal image to obtain the region above the position p of the breast region and the region below the position q of the breast region is as per the thermal imaging protocol; and adjust at least one of the position of the thermal imaging camera, the position of the subject or the position of the subject chair in a left direction or a right direction to capture the new adjusted thermal image to obtain the position r of the distance of the breast region from either of the first or the last pixel column is as per the thermal imaging protocol.

13. The system of claim 11, wherein the system provides the new adjusted captured thermal image along with the position adjustment for an automatic tumor detection or an automatic tumor classification to detect cancerous tissue and non-cancerous tissue within the breast region of the subject.

14. The method of claim 11, wherein a detected breast region segment in the new adjusted captured thermal image is provided for an automatic tumor detection or an automatic tumor classification to detect cancerous tissue and non-cancerous tissue within the breast region of the subject, if the plurality of deviations does not exceed a threshold value as per the thermal imaging protocol.

15. The system of claim 11, wherein the system provides a set of instructions to at least one of a robotic arm holding the camera, electronically controlled camera stand, electronically controlled rotating chair to automatically positions to a suggested position adjustment for capturing the new adjusted thermal image of the body of the subject as per the thermal imaging protocol, wherein the set of instructions are generated by the machine learning model based on the positional adjustment.

* * * * *